United States Patent [19]

Bellasio et al.

[11] 4,247,551
[45] Jan. 27, 1981

[54] N-PYRROLYL-PYRIDAZINEAMINES AND THEIR USE AS ANTIHYPERTENSIVE AGENTS

[75] Inventors: Elvio Bellasio, Como; Nunzio Di Mola, Milan; Ambrogio Campi, Monza; Emiliana Baldoli, Milan, all of Italy

[73] Assignee: Gruppo Lepetit S.p.A., Milan, Italy

[21] Appl. No.: 76,114

[22] Filed: Sep. 17, 1979

[51] Int. Cl.$^3$ ................. A61K 31/50; A61K 31/535; C07D 403/12; C07D 413/14

[52] U.S. Cl. ............................. 424/248.56; 424/246; 424/248.54; 424/250; 544/58.6; 544/60; 544/62; 544/114; 544/116; 544/237; 544/238

[58] Field of Search ............... 544/114, 116, 58.6, 544/60, 62, 238, 237; 424/246, 248.54, 248.55, 248.56, 250

[56] References Cited

FOREIGN PATENT DOCUMENTS

| | | |
|---|---|---|
| 1157642 | 7/1969 | United Kingdom . |
| 1299421 | 12/1972 | United Kingdom . |
| 1373548 | 11/1974 | United Kingdom . |
| 1408362 | 10/1975 | United Kingdom . |

OTHER PUBLICATIONS

E. Jucker, *Progress in Drug Research*, vol. 20, pp. 203–205 (1976), vol. 4, p. 332 (1962).
E. Bellasio et al., *Il Farmaco Ed. Sch.*, vol. 24, p. 919 (1969).
G. Pifferi et al., *J. Med. Chem.*, vol. 18, p. 741 (1975).

*Primary Examiner*—Alan L. Rotman
*Assistant Examiner*—R. W. Ramsuer

[57] ABSTRACT

New-pyrrolyl-3-pyridazineamines having a further aminic substituent in the position 6. The compounds are useful as antihypertensive agents and may be prepared from 6-amino substituted-3-hydrazino pyridazines and β-dicarbonyl compounds. The use of the novel compounds as antihypertensives and compositions containing the novel compounds as active ingredients are also claimed.

11 Claims, No Drawings

N-PYRROLYL-PYRIDAZINEAMINES AND THEIR USE AS ANTIHYPERTENSIVE AGENTS

FIELD OF THE INVENTION

The invention relates to new N-pyrrolyl-pyridazineamines derivatives having antihypertensive activity, to the process for their manufacture and to their use as antihypertensive agents.

BACKGROUND OF THE INVENTION 2-(Pyrrol-1-yl)-imidazoleamines having antihypertensive effectiveness are known from U.K. Pat. No. 1408362. 3-Hydrazinopyridazines and 4-hydrazinophthalazines having antihypertensive activity are broadly described in the pharmaceutical literature (see Progress in Drug Research, Vol. 20, pages 203–205, edited by E. Jucker, Birkhäuser Verlag Basel, 1976).

The prior literature teaches that blocking of the terminal nitrogen of hydrazine moiety of the 4-hydrazinophthalazines through chemically stable substituents such as alkyl or aryl groups leads to virtually inactive compounds (see Progress in Drug Research, Vol. 4, page 332, edited by E. Jucker, Birkhäuser Verlag, Basel, 1962).

SUMMARY OF THE INVENTION

The novel compounds which form the first object of this invention are N-pyrrolyl-pyridazineamine derivatives of the general formula

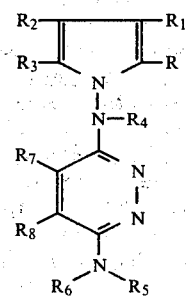

wherein R, $R_1$, $R_2$, $R_3$, may be the same or different and are independently selected from hydrogen and lower alkyl; $R_4$ represents hydrogen, lower alkyl, lower alkylamino-lower alkyl, di-lower alkylamino-lower alkyl, lower alkanoyl, halo-lower alkanoyl, carbo(lower alkoxy) or carbobenzyloxy; $R_5$ and $R_6$ each independently represent lower alkyl, hydroxy-lower alkyl, lower alkoxylower alkyl, lower alkanoyloxy-lower alkyl, lower alkenyl, phenyl, substituted phenyl, phenyl-lower alkyl and substituted phenyl-lower alkyl or taken together with the adjacent nitrogen atom represent a saturated 5-6 membered heterocyclic ring which may contain a further heteroatom selected from O, N and S, and which may bear 1 to 2 substituents selected from lower alkyl, phenyl, substituted phenyl, phenyl-lower alkyl, substituted phenyl-lower alkyl, hydroxy, hydroxy-lower alkyl, and lower alkanoyloxy; $R_7$ and $R_8$ represent hydrogen atoms or, taken together, a 1,3-butadienylene radical forming a benzo system fused with the pyridazine ring.

The invention includes the pharmaceutically acceptable acid addition salts of the compounds of formula (I). In the specification and in the claims the term "lower alkyl" designate a $C_1$-$C_4$ straight or branched alkyl, preferably methyl and ethyl; the term "lower alkoxy" designate an alkoxy group wherein the aliphatic portion is a straight or branched alkyl of 1 to 4 carbon, preferably a methoxy or an ethoxy group; the term "lower alkanoyl" designates an alkanoyl radical of 1 to 4 carbons, preferably acetyl and propionyl, the term "halo-lower alkanoyl" designates a lower alkanoyl of 2 to 4 carbon atoms with 1 to 3 halo substituents, preferably chloroacetil, fluoroacetil, trichloroacetil and trifluoroacetil; the term "hydroxy-lower alkyl" designates a lower alkyl of 1 to 4 carbon atoms with a hydroxy substitution on the chain, preferably, 2-hydroxyethyl,2-hydroxypropyl and 3-hydroxypropyl; the terms "lower alkylamino-lower alkyl" and "di-lower alkylamino-lower alkyl" designate lower alkyls of 1 to 4 carbon atoms having one ($C_1$-$C_4$)alkylamino or di-($C_1$-$C_4$)alkylamino substituent such as, for instance, methylamino, dimethylamino, ethylamino and diethylamino; the term "lower alkanoyloxy" designates an alkanoyloxy group of 1 to 4 carbon atoms, preferably formyloxy, acetyloxy and proprionyloxy; the term "lower alkoxy-lower alkyl" designates a group wherein the lower alkoxy portion is defined as before and the lower alkyl portion is an alkyl of 1 to 4 carbon, preferably ethyl and propyl; the term "lower alkanoyloxy-lower alkyl" designates a group wherein the lower alkanoyloxy portion is defined as before and the lower alkyl portion is an alkyl of 1 to 4 carbon, preferably ethyl and propyl; the term "lower alkenyl" designates an alkenyl of 3 to 4 carbon atoms, preferably allyl; the term "substituted phenyl" represents a phenyl substituted with 1 to 3 substituents independently selected from, chloro, fluoro, bromo, lower alkyl, hydroxy, lower alkoxy and methylenedioxy, preferably chlorophenyl, tolyl, methoxyphenyl, dimethoxyphenyl, trimetoxyphenyl, and 3,4-methylenedioxyphenyl; the term "substituted phenyl-lower alkyl" designates a group wherein the substituted phenyl portion is as defined before and the lower alkyl portion is a 1 to 4 carbon alkyl, preferably methyl and ethyl; representative members of the "saturated 5-6 membered heterocyclic rings which may contain a further heteroatom selected form N, O and S", are pyrrolidine, piperidine, piperazine, morpholine and thiomorpholine; typical examples of substitutions on said heterocyclic rings include lower alkyl, hydroxy, hydroxy-lower alkyl and lower alkanoyloxy substituents on the carbon atom moiety of said rings and/or lower alkyl, hydroxy-lower alkyl, phenyl, substituted phenyl, phenyl-lower alkyl, substituted phenyl-lower alkyl substituents on the second nitrogen atoms when the ring contains said further heteroatom.

The phrase "pharmaceutically acceptable acid addition salts" refers to non toxic acid addition salts of the compounds the anion of which are relatively innocuous to animals at dosages consistent with good antihypertensive activity so that the beneficial pharmacological effect is not vitiated by the side effects ascribable to the anions.

Pharmacologically-acceptable salts include those derived from mineral acids such as hydrochloric acid, hydrobromic acid, sulfuric acid as well as those derived from organic acids such as lactic, maleic, succinic, fumaric, oxalic, glutaric, citric, malic, tartaric, p-toluenesulfonic, benzenesulfonic, methanesulfonic, cycloexanesulfonic acid and the like.

The use of novel N-pyrrolyl-pyridazineamines as anti-hypertensive agents refers to all industrially applicable aspects and acts of said use, including the embodying of the novel compounds into pharmaceutical compositions. The pharmaceutical compositions containing said active compounds are in fact a further specific object of this invention.

The compounds and the compositions of this invention are useful as antihypertensive agents, that is, when said substances are administered in pharmacologically effective amounts to animals suffering of spontaneous or experimentally induced hypertension, produce a considerable reduction of the blood pressure, without displaying any untolerable side effect. The compounds of this invention have the peculiar characteristic of a long lasting action since a remarkable reduction of the blood pressure in the test animals is still persistent even seven hours after administration.

The process for the manufacture of the novel N-pyrrolyl-pyridazineamines of this invention comprises contacting a hydrazino derivative of the formula

wherein $R_4$, $R_5$, $R_6$, $R_7$ and $R_8$ have the same meanings as above or an acid addition salt thereof with a dicarbonyl compound of the formula

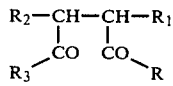

wherein R, $R_1$, $R_2$ and $R_3$ have the same meanings as above or a functional derivative thereof wherein the keto functions can be easily restored under the reaction conditions. The two reactants are usually contacted in about equimolecular amounts although a 1% to 20% excess of dicarbonyl compound may in some instances positively affect the conversion yields of the hydrazine compound.

The reaction is usually carried out in the presence of a solvent such as water, a $C_1$-$C_4$ alkanol, acetic acid, benzene, toluene, tetrahydrofuran, dioxane and mixture thereof, preferably in the presence of an acidic catalyst.

Although several type of catalysts such as hydrohalic acids, sulfuric acid, p-toluenesulfonic acid and Lewis acids may be employed, lower alkanoic acids are particularly suitable in that they may be used simultaneously both as solvents and catalysts. Among the lower alkanoic acids, acetic acid is particularly preferred.

In the case where an acid addition salt of the hydrazine of the formula (2) is employed, such as the hydrohalides, the di-hydrohalides, the sulfate and the hydrogen sulfate, the addition of a base or of a basic buffering agents to the reaction solution is needed to allow reaction of the hydrazine in the free base form.

The reaction temperature is generally ranging between about 10° C. and the boiling temperature of the reaction mixture, preferably between 15° C. and 120° C., most preferably between 20° C. and 85° C.

The reaction time may vary from about 0,5 to about 4 hours during which the reaction course may be monitored by thin layer chromatography.

The recovery of the reaction product is carried out according to the general procedures for recovering solid or oily products from organic solutions.

In generic operations, once the reaction is completed, the reaction solution is evaporated to dryness, the residue is slurried with an aqueous solution of a base to remove traces of the acidic catalyst (or solvent); the residue may be dissolved in an organic solvent and then recovered by concentration and/or cooling of the organic solution. The compound thus obtained may be further purified by usual procedures such as crystallization from solvents, column chromatography, preparative thin layer chromatography and similar methods.

The acid addition salts of the compounds of formula (I) may be obtained through commonprocedures from the corresponding free basesby addition of an appropriate acid.

The intermediate hydrazines of formula (II) are prepared according to procedures described in the literature. Some hydrazino-pyridazines are specifically described for instance in the following U.K. patents: U.K. Pat. No. 1.157.642, U.K. Pat. No. 1.373.548, U.K. Pat. No. 1.299.421 and in the following papers: E. Bellasio et al. Il Farmaco Ed. Sci. 24, 919 (1969); G. Pifferi et al. J. Med. Chem. 18, 741 (1975).

For preparation of compounds of formula (I) wherein $R_4$ represents lower alkyl, lower alkanoyl, carbo(lower alkoxy), or carbobenzyloxy, besides the general method described above, a further procedure may be advantageously employed in cases where the preparation of the corresponding N-alkylated or acylated hydrazine starting material is difficult. This alternative procedure involves preparation of the compounds of formula I wherein $R_4$ is hydrogen which is then alkylated or acylated on the unsubstituted nitrogen-atom by means of common alkylation or acylation procedures.

Alkylation may be carried out, for instance, with lower alkyl halides or sulfates in the presence of acid acceptors such as alkali metal hydrides, alkali metal alkoxydes and the like. Acylation may be carried out by reacting the N-unsubstituted compound with the appropriate acyl halide or anhydride, optionally in the presence of an acid acceptor such as pyridine.

The acylation procedure may also be employed for conversion of free hydroxy groups to lower acyloxy in the portion

of the compounds of formula (I) above. Representative example of compounds of this invention are indicated in TABLE I.

The antihypertensive activity of the compounds of the invention was shown in representative tests on spontaneous hypertensive rats and in renal hypertensive dogs. In representative experiments with renal hypertensive dogs, effective amounts (1 to 4 mg/kg) of compounds of examples 3, 4, 5, 6, 8, 13, 14 and 15 were administered p.o. to the conscious hypertensive animals. The systolic arterial blood pressure was measured by the indirect method on the tail before and 1, 3, 5 and 7 hours after treatment.

The results of these experiments showed that the compounds were effective in lowering the blood pressure. The drop of the systolic blood pressure ranged between 20 and 70 mm Hg, depending on the specific compound tested and on the time at which the blood pressure was observed. In general the antihypertensive effect started about 3 hours after treatment and the maximum effect was still persistent 7 hours after treatment.

In representative experiments with spontaneous hypertensive rats (MHR: Milano hypertensive rats; see G. Bianchi et al.—Clinical and Experimental Pharmacology and Phiosiology, Suppl. 3, 15–20, 1976) a 20 to 60 mm Hg systolic blood pressure drop was observed in the test animals administered p.o. with effective (2 to 100 mg/kg) amounts of the compounds of Examples 1, 2, 3, 4, 5, 6, 7, 8, 9, 11, 12, 13, 14, 15, 16, 17, 18, 19, 20, 21, 22, 23, 25 and 26.

The toxicity of these compounds was found to be very low since the values of the $LD_{50}$ in mice were generally higher than 500 mg/kg p.o. and, in most cases, the $LD_{50}$ was greater than 800 mg/kg p.o. Besides, representative compounds of this invention have shown absence of any mutagenic effect in current mutagenetic in vitro tests (See Ames et al.: Proc. Natl. Acad. Sci. U.S., 70:782, 1973).

For instance, the compound of example 3 having a value of $LD_{50}$ of about 800/kg p.o. provoked a blood pressure drop of 38 mm Hg, when administered at a dose of 5 mg/kg to spontaneous hypertensive rats. In renal hypertensive dogs, drops of the systolyc blood pressure of 50 and 70 mm Hg, were observed with doses of 1 and 4 mg/kg p.o. respectively. The hydrochloride of said compound of example 3 as well as the compounds of examples 2, 19 and 21 showed analogous results.

A surprising and very interesting pharmacological effect showed by these compounds is the persistence of the antihypertensive action even at a considerable period of time after the administration. For instance, the compound of example 3, when administered at a dose of 2 mg/kg to renal hypertensive dogs, showed a maximum systolic blood pressure drop of 52 mm Hg after about three hours and after seven hours a blood pressure drop of 48 mm Hg was still registered. Under the same conditions and at the same dosage, hydralazine (1-hydrazinophthalazine) showed a maximum decrease of the systolic blood pressure of 41 mm Hg after about one hour but, after seven hours, the blood pressure decrease was only of 29 mm Hg.

The effect was confirmed in experiments wherein the two substances were administered intravenously at equipotent dosages.

Another very remarkable effect of the antihypertensive compounds of this invention is that the maximum blood pressure drop is reached through a gradual decrease which does not dramatically affect all the circulatory parameters concerned, thus avoiding the undesired side-effects generally displayed by most of the known antihypertensive substances.

The persistance of the antihypertensive effect is a very favorable characteristic of the novel compounds of this invention, since it allows a less frequency administration schedule and, moreover, the total amount of antihypertensive substance required to keep the blood pressure value at a normal level in chronically hypertensive patients is lower than with other hypertensive substances having the same potency but with a shorter period of action.

DETAILED DESCRIPTION OF THE INVENTION

The following are examples of preparation of representative compounds of this invention given by way of illustration only, without any intention of limiting the present invention.

EXAMPLE 1

N-(2,5-Diethyl-1H-pyrrol-1-yl)-6-morpholino-3-pyridazineamine

To 1.95 g (10 m moles) of 3-hydrazino-6-morpholino-pyridazine dissolved in 12 ml of acetic acid, 1.71 g (12 m moles) of 3,6-octanedione dissolved in 4 ml of acetic acid are added at room temperature. The mixture is heated at 67° C. for 2 hours and then evaporated to dryness under vacuum. The oily residue is dissolved in toluene and the solution is evaporated to dryness. The residue is slurried with ice-water and neutralized with sodium bicarbonate to yield 2.58 g of a solid product. Said material, after crystallization from isopropanol gives 1.25 g (42%) of the title product, melting at 186°–9° C. Elemental analysis, I. R., N.M.R. and mass spectra are in agreement with the assigned structure.

EXAMPLE 2

6-Diethylamino-N-(2,5-dimethyl-1H-pyrrol-1-yl)-3-pyridazineamine

To 105 ml of acetic acid, 15.3 g (60 m moles) of 6-diethylamino-3-hydrazino-pyridazine dihydrochloride, 9.85 g (120 m moles) of sodium acetate and 7.51 g (66 m moles) of 2,5-hexanedione are added and the mixture is heated at 67° C. for 3.5 hours.

The solvent is evaporated off under vacuum yielding an oily residue which is dissolved in toluene. The toluene solution is evaporated and the residue obtained, is slurried with ice-water and neutralized with a saturated sodium carbonate solution. After extraction of the mixture with three portions of 150 ml of chloroform, the organic layer is washed with water and evaporated in vacuo to yield 17 g of crude product. Said material is purified by chromatography through a silicagel column by eluting with cyclohexane-ethyl acetate mixtures wherein the ratio of ethyl acetate to cyclohexane is gradually increased from 1:4 to 1:1.

By evaporation of the eluate 6 g (39%) of the product of the title are obtained. After crystallization from isopropanol the compound melts at 148°–150° C.

Elemental analysis, I.R. and N.M.R. data are in agreement with the assigned structure.

EXAMPLE 3

N-(2,5-Dimethyl-1H-pyrrol-1-yl)-6-morpholino-3-pyridazineamine (a) 8.25 Grams (42.3 m moles) of 3-hydrazino-6-morpholino pyridazine and 5.82 g (51 m moles) of 2,5-hexanedione in 40 ml of acetic acid are heated at 67° C. for 3.25 hours. The solvent is evaporated off under vacuum and the residue is slurried with ice-water and neutralized with aqueous sodium carbonate.

The product is purified through column chormatography on silicagel by eluting with cyclohexane-ethyl acetate mixtures wherein the ratio of ethyl acetate to cyclohexane is gradually increased from 1:4 to 2:1. The fractions containing the purified product are combined and evaporated to dryness giving a solid residue which, after crystallization from isopropanol, melts at 191°–193° C. (yield 6 g, 52%).

Elemental analysis, I.R. and N.M.R. data are in agreement with the assigned structure.

(b) The same compound is obtained also by following the procedure of example 2 using 14 g of 3-hydrazino-6-morpholino-pyridazine dihydrochloride, 8.6 g of sodium acetate and 6.52 g of 2,5-hexanedione in 90 ml of acetic acid. The yield is 9.5 g (48%) of the product of the above title.

(c) A further procedure to prepare the compound of the title is the following:

To 58.6 g (200 m mol) of 6-hydrazino-3-(4-morpholino)-pyridazine sulfate dissolved in 100 ml of water, 200 ml of 1 N sodium hydroxide are gradually added under cooling and when this addition is completed, 25 g (220 m mol) of 2,5-hexanedione are added to the mixture which then is heated at 70° C. for four hours. After cooling to about 20° C., a further addition of 200 ml of 1 N sodium hydroxide is made and the product precipitated is removed by filtration and washed on filter with three portions of 100 ml of ice-water. After drying at 50° C. over $P_2O_5$ the solid weights 54.4 g (99%). The product shows satisfactory analytical characteristics. The 6-hydrazino-3-(4-morpholino)-pyridazine sulfate is obtained by adding the stoichiometric amount of $H_2So_4$ to an aqueous solution of the hydrazine and evaporating off the water. The sulfate melts at 202°–4° C. when crystallized from ethanol containing 10% of water. The hydrochloride of the compounds of the title is obtained by dissolving 17 g of the free base in 150 ml of absolute ethanol at 70° C. and then adding to said solution 45 ml of ethyl ether saturated with hydrogen chloride. Further addition of 300 ml of ethyl ether to the cooled solution yields a precipitate which after filtration is crystallized from 200 ml of 85% ethanol. Yield 13.5 g; the compounds decomposes at 260° C.

EXAMPLE 4

6-(2,6-Dimethyl-morpholino)-N-(2,5-dimethyl-1H-pyrrol-1-yl)-3-pyridazineamine

The compound is prepared according to the procedure of example 2 by contacting 3.8 g (12.8 m moles) of 6-(2,6-dimethyl-morpholino)-3-hydrazino-pyridazine dihydrochloride (prepared according to the procedure described in U.K. Pat. No. 1.157.642; m.p. 217°–220° C.), 2.2 g (25.6 m moles) of sodium acetate and 1.61 g (14.1 m moles) of 2,5-hexanedione in 20 ml of acetic acid. The yield is 1.8 g (47%) of the product of the title which melts at 147°–148° C. when crystallized from ethyl ether.

Elemental analysis, I.R. and N.M.R. data are in agreement with the assigned structure.

EXAMPLE 5

N-(2,5-Dimethyl-1H-pyrrol-1-yl)-4-morpholino-1-phthalazineamine

To 4.9 grams (20 m moles) of 1-hydrazino-4-morpholino phthalazine (prepared from 1,4-dichlorophthalazine) according to the procedure of U.K. Pat. No. 1.157.642; M.p. 255°–260° C.) dissolved in 30 ml of acetic acid, 2.74 g (24 m moles) of 2,5-hexanedione are added and the mixture is heated at 65° C. for 3 hours.

The solvent is evaporated off under vacuum and the residue is slurried with water and neutralized with a saturated solution of sodium carbonate. The row product is extracted with ethyl acetate and the organic solution, after washing with water and drying over $CaSO_4$ is evaporated to dryness. The residual product is purified by chromatography through a silicagel column using cyclohexane-ethyl acetate 1:3 as the eluent. Evaporation of the eluate, yields 2.7 g (47%) of the product of the title which after crystallization from acetone, melts at 205°–209° C.

Elemental analysis, I.R. and N.M.R. data are in agreement with the assigned structure.

EXAMPLE 6

6-Diallylamino-N-(2,5-dimethyl-1H-pyrrol-1-yl)-3-pyridazineamine

To 7 g (25 m moles) of 6-diallylamino-3-hydrazino-pyridazine dihydrochloride (Ger. Appl. 2.002.107; C.A. 73, 66596, 1970), and 4.1 g (50 m moles) of sodium acetate dissolved in 40 ml of acetic acid, 3.42 g (30 m moles) of 2,5-hexanedione are added.

After heating for 4 hours at 65° C., the mixture is evaporated to dryness. The residue is slurried with ice-water and neutralized with sodium carbonate. The mixture is extracted with ethyl acetate and the row product obtained by evaporayion of the organic extract (7 g) is purified by chromatography through a silicagel column using chloroform and a mixture chloroform-methanol 98.5:1.5 as the eluent. Evaporation of the eluate yields a product which, after crystallization from ethyl ether, melts at 135°–136° C. (2.6 g, 37%).

Elemental analysis, I.R. and N.M.R. data are in agreement with the assigned structure.

EXAMPLE 7

N-(2,5-Dimethyl-1H-pyrrol-1-yl)-6-(1-pyrrolidinyl)-3-pyridazineamine

To a mixture of 5.2 g (20.7 m moles) of 3-hydrazino-6-(1-pyrrolidinyl)pyridazine dihydrochloride (prepared according to U.K. Pat. No. 1.157.642. The compound was characterized through the dihydrochloride of the corresponding hydrazone with acetone melting at 215°–220° C.) and 3.56 g (43 m moles) of sodium acetate in 60 ml of acetic acid, 2.74 g (24 m moles) of 2,5-hexanedione are added. After stiring for 3 hours at 65°–55° C. the solvent is evaporated off under vacuum.

The residue is slurried with water, neutralized with sodium bicarbonate and then dissolved in chloroform. The chloroform solution is chromatographed through silicagel by eluting with cyclohexane-ethyl acetate mixtures wherein the ratio of ethyl acetate to cyclohexane is gradually increased from 1:1 to 4:1. The eluate is evaporated to dryness and the solid residue is crystallized from ethyl acetate yielding 3.35 g (63%) of the product of the title which melts at 208°–209° C.

Elemental analysis, I. R. and N.M.R. data are in agreement with the assigned structure.

EXAMPLE 8

N-(2,5-Dimethyl-1H-pyrrol-1-yl)-6-piperidino-3-pyridazineamine

A mixture of 7.4 g (28 m moles) of 3-hydrazino-6-piperidino-pyridazine, 2.3 g of sodium acetate and 3.7 g 2,5-hexanedione is heated for two hours at 65° C. The solvent is evaporated off under vacuum and the solid residue is dissolved in water and neutralized with sodium hydroxide. The product is purified by chromatography through a silicagel column using as the eluent a mixture methanol-chloroform 2.5:97.5. The solid recovered by evaporation of the eluate is crystallized from ethyl acetate yielding 2 g (27%) of the product of the title which melts at 185°-187° C.

Elemental analysys; I.R. and N.M.R. data are in agreement with the assigned structure.

EXAMPLE 9

N-(2,5-Dimethyl-1H-pyrrol-1-yl)-6-(4-methyl-1-piperazinyl)-3-piridazineamine.

A mixture of 7 g (35 m moles) of 3-hydrazino-6-(4-methyl-1-piperazinyl)-pyridazine and 4.1 g (36 m moles) of 2,5-hexanedione in 100 ml of acetic acid is heated for 3 hours at 70° C. The solvent is evaporated off under vacuum and the oily residue is dissolved in water and made alkaline with 10% sodium hydroxyde. The mixture is extracted with ethyl acetate and the organic layer is evaporated to dryness in vacuo. The solid residue is crystallized first from ethyl ether and then from ethyl acetate yielding 2.6 g (26%) of the product of the title which melts at 181°-182° C.

Elemental analysis, I.R. and N.M.R. data are in agreement with the assigned structure.

EXAMPLE 10

N-(2,5-Dimethyl-1H-pyrrol-1-yl)-6-(1-piperazinyl)-3-pyridazineamine

A mixture of 9.2 g (40 m moles) of 3-hydrazino-6-(1-piperazinyl)-pyridazine hydrochloride (m.p. 257° C.; prepared according to the procedure of U.K. Pat. No. 1.157.642), 3.28 g (40 m moles) of ethyl acetate and 4.82 g of 2,5-hexanedione in 100 ml of acetic acid is heated at 75° C. for 2 hours and then allowed to stand for two days at room temperature.

After filtration, the solvent is evaporated off in vacuo and the residue is dissolved in water and made alkaline with 10% sodium hydroxide. Extraction with ethyl acetate and evaporation of the organic layer, yields 4.1 g of crude product which is purified by chromatography through a silicagel column using a methanol-chloroform 7:3 as the eluent. Yield 3 g (28%) of a the title product which after crystallization from acetonitrile melts at 189°-191° C.

Elemental analysis, I.R. and N.M.R. data are in agreement with the assigned structure.

EXAMPLE 11-15

The following products are prepared by contacting the corresponding hydrazinopyridazines dihydrochlorides and 2,5-hexanedione in the presence of ethyl acetate according to the procedure described in example 2.

(11) N-(2,6-Dimethyl-1H-pyrrol-1-yl)-6-[N',N'-bis(2-hydroxyethyl)amino]-3-pyridazineamine. M.p. 128°-130° C. Yield 65%.

(12) N-(2,6-Dimethyl-1H-pyrrol-1-yl)-6-[N'-(2-hydroxyethyl)-N'-(2-hydroxypropyl)amino]-3-pyridazineamine. M.p. 129°-131° C. Yield 40%.

(13) N-(2,6-Dimethyl-1H-pyrrol-1-yl)-6-[N'-(2-hydroxyethyl)-N'-methyl-amino]-3-pyridazineamine. M.p. 139°-140° C. Yield 64%.

(14) N-(2,6-Dimethyl-1H-pyrrol-1-yl)-6-[N',N'-bis(2-hydroxypropyl)amino]-3-pyridazineamine. M.p. 137°-139° C. Yield 45%.

(15) N-(2,6-Dimethyl-1H-pyrrol-1-yl)-6-(4-hydroxy-piperidino)-3-pyridazineamine. M.p. 175°-177° C. Yield 30%.

The starting hydrazino-pyridazine compounds of examples 11 to 15 are literature compounds. The starting material of example 15 was prepared according to the procedure described in U.K. Pat. No. 1.157.642 and was employed as such for the further reaction without isolation and characterization.

EXAMPLE 16

N-(2,5-Dimethyl-1H-pyrrol-1-yl)-N-methyl-6-morpholino-3-pyridazineamine.

To 1.36 g (5 m moles) of N-(2,5-dimethyl-1H-pyrrol-1-yl)-6-morpholino-3-pyridazineamine in 13.6 ml of dimethylformamide, 0.26 g (5.5 m moles) of 55% sodium hydride are added. The mixture is stirred for 30 minutes at room temperature and for additional 30 minutes at 55° C. Then, a solution of 0.78 g (5.5 m moles) of methyl iodide in 2 ml of dimethylformamide is gradually added at 10° C. When the addition is completed the mixture is heated at 50° C. for 45 minutes. The dimethylformamide is evaporated off in vacuo and the residue is dissolved in ethyl acetate. The organic layer is washed with water and then evaporated to dryness to give a solid which is crystallized from hexane. Yield 0.7 g (54%) of the product of the title which melts at 119°-122° C.

Elemental analysis, I.R. and N.M.R. data are in agreement with the assigned structure.

EXAMPLE 17

N-Acetyl-N-(2,5-dimethyl-1H-pyrrol-yl)-6-morpholino-3-pyridazineamine

A mixture of 6 g (22 m mol) of N-(2,5-dimethyl-1H-pyrrol-yl)-6-morpholino-3-pyridazineamine, 30 ml of acetic anhydride, and 6 ml of pyridine is heated for one hour at 110° C. The reaction mixture is evaporated to dryness under vacuum and the oily residue is dissolved in 150 ml of ethyl acetate. The organic solution is washed first with 50 ml of an aqueous solution of sodium bicarbonate and then with 50 ml of water.

The organic layer is dryed over Ca SO4 and evaporated to yield an oily residue which is chromatographed on a silicagel column using cyclohexane-ethyl acetate 3:2 as the eluent.

After evaporation of the eluate the oily residue dissolved in ethyl ether is additioned with a hydrogen chloride ethyl ether solution.

The solid precipitate, which is highly hygroscopic, is recovered by filtration and crystallized from isopropanol-ethyl ether 1:1. Yield 4.9 g (64%) of the product of the title melting at 162°-68° C.

Elemental analysis, I.R. and N.M.R. data are in agreement with the assigned structure.

EXAMPLE 18

N-(2,5-Dimethyl-1H-pyrrol-1-yl)-6-(4-thiomorpholinyl)-3-pyridazineamine

3-Hydrazino-6-(4-thiomorpholinyl)-pyridazine dihydrochloride and 2,5-hexanedione are reacted in acetic acid in the presence of sodium acetate according to the procedure of example 2. The product is recovered by evaporating the acetic acid and slurring the residue in aqueous sodium bicarbonate. The solid obtained after filtration is purified by chromatography through silicagel using a chloroform-methanol mixture 97.5:2.5 mixture as the eluent. Yield 50%. M.p. 203° C. (from ethyl acetate). Elemental analysis, I.R. and N.M.R. data are in agreement with the assigned structure.

EXAMPLE 19

N-(2,5-Dimethyl-1H-pyrrol-1-yl)-6-[N',N'-bis(2-methoxyethyl)amino]-3-pyridazineamine The compound is obtained according to the same procedure described in example 2 by reacting 3-hydrazino-6-[N,N-bis(2-methoxyethyl)amino]-pyridazine dihydrochloride and 2,5-hexanedione in acetic acid in the presence of sodium acetate. The chromatographic purification or a silicagel column is carried out by using a mixture ethyl acetate-cyclohexane 3:1 as the eluent. Yield 60% M.p. 112°–14° C. (from ethyl acetate).

The 3-hydrazino-6-[N,N-bis(2-methoxyethyl)amino]-pyridazine dihydrochloride, m.p. 198°–200° C., is obtained by employing the procedures of methods E, F, G described by G. Pifferi et al. in J. Med. Chem., 18, 741 (1975).

EXAMPLE 20

N-(2,5-Dimethyl-1H-pyrrol-1-yl)-6-[N'-methyl-N'-(2-methoxyethyl)amino]-3-pyridazineamine The compound is prepared according to the procedure of example 19 from 3-hydrazino-6-[N-metyl-N-(2-methoxyethyl)amino]-pyridazine dihydrochloride and 2,5-hexanedione in acetic acid in the presence of sodium acetate. Yield 55%. M.p. 106° C. (from ethyl ether). The dihydrochloride of 3-hydrazino-6-[N-methyl-N-(2-methoxyethyl)amino]-pyridazine, m.p. 219°–221° C., is obtained by employing the procedures of methods E, F, G described by G. Pifferi et al. in J. Med. Chem., 18, 741 (1975).

EXAMPLE 21

N-(2,5-Dimethyl-1H-pyrrol-1-yl)-6-[N',N'-bis(2-ethoxyethyl)amino]-3-pyridazineamine The compound is prepared according to the procedure of example 19, from 3-hydrazino-6-[N,N-bis(ethoxyethyl)amino]-pyridazine dihydrochloride and 2,5-hexanedione in acetic acid, in the presence of sodium acetate. Yield 70%. B.p. 180° C./0.2 mm Hg. The dihydrochloride of 3-hydrazino-6-[N,N-bis(ethoxyethyl)amino]-pyridazine, m.p. 181°–183° C., is obtained by employing the procedures of methods E, F, G described by G. Pifferi et al. in J. Med. Chem., 18, 741 (1975).

EXAMPLE 22

N-(2,5-Dimethyl-1H-pyrrol-1-yl)-6-dimethylamino-3-pyridazineamine

The product is obtained according to the procedure of example 19 by reacting 3-hydrazino-6-dimethylamino-pyridazine dihydrochloride and 2,5-hexanedione in acetic acid in the presence of sodium acetate. Yield 47%; m.p. 165°–167° C. (from ethyl ether).

EXAMPLE 23

N-(2,5-Dimethyl-1H-pyrrol-1-yl)-6-[4-(2-methoxyphenyl-1-piperazinyl]-3-pyridazineamine The product is obtained according to the procedure of example 19 by reacting 3-hydrazino-6-[4-(2-methoxyphenyl-1-piperazinyl]-pyridazine and 2,5-hexanedione in acetic acid in the presence of sodium acetate. Yield 51%, m.p. 194°–196° C. The starting hydrazine was prepared from 3,6-dichloropyridazine according to the process described in U.K. Patent 1.157.642. The 3-chloro-6-[4-(2-methoxyphenyl)-1-piperazinyl]-pyridazine intermediate melts at 141°–143° C. The hydrazine was not characterized as a free base but was employed as such for the reaction with 2,5-hexanedione. The benzilidene hydrazone of said hydrazine melts at 230°–233° C. (from methanol).

EXAMPLE 24

6-Morpholino-N-(1H-pyrrol-1-yl)-3-pyridazineamine

To 5.85 g (30 m mol) of 3-hydrazino-6-morpholino-pyridazine in 130 ml of ethanol, ethyl ether (45 ml) saturated with hydrogen chloride is added. The suspension of pale yellow precipitate which forms is additioned with 12 g (90 m mol) of 2,5-dimethoxytetrahydrofuran and the mixture is refluxed (60° C.) for 6 hours. The solvent is removed under vacuum and the residue is dissolved in water, brought to pH 8 by addition of a sodium carbonate solution and extracted with four portions (each of 100 ml) of dichloromethane. The organic extracts are pooled together, washed with water (50 ml) and anhydrified over sodium sulfate. Evaporation of the solvent yields an oil which is purified through column chromatography (silicagel, 500 g) using as the eluent a mixture of dichloromethane and ethyl acetate wherein the ratio of ethyl acetate is gradually increased from 20% to 100%. Evaporation of the more polar fraction yields 0.15 g (2%) of the product of the title which melts at 228° C.

Elemental analysis, I.R. and N.M.R. data confirm the assigned structure.

EXAMPLE 25

N-Methyl-6-morpholino-N-(1H-pyrrol-1-yl)-3-pyridazineamine

To a solution of 6.76 g (22.5 m mol) of 3-(1-methylhydrazino)-6-morpholino-pyridazine dihydrochloride monohydrate in 135 ml of ethanol, a saturated solution of hydrogen chloride in ethyl ether (18 ml) and 4.46 g (33.75 m mol) of 2,5-dimethoxytetrahydrofuran are added. After refluxing for 3 hours, the solvent is evaporated off under vacuum and the residue, dissolved in water is neutralized with aqueous sodium bicarbonate. After extraction with three portions (each of 200 ml) of dichloromethane, the extracts are combined and anhydrified over sodium sulfate. Evaporation of the solvent yields a product which is purified through a silicagel column (350 g) using a mixture ethyl acetate-cyclohexane 1:3 as the eluent. Crystallization from ethyl ether yields 2.31 g (50%) of the product of the title, which melts between 105° and 117° C. (Thermal analysis shows that two crystalline forms are present, one melting at 105° C. and the other at 117° C.).

Elemental analysis, I.R. and N.M.R. data confirm the assigned structure.

The 3-(1-methylhydrazino)-6-morpholino-pyridazine dihydrochloride monohydrate is prepared through the following procedure:

The hydrazone of 3-hydrazino-6-morpholino-pyridazine with acetaldehyde is prepared from 3-hydrazino-6-morpholino-pyridazine and acetaldehyde in water solution; m.p. 175°–180° C. The hydrazone, after drying, is heated (55° C., 30 minutes) with a slight excess of 55% sodium hydride in dimethylformamide. To the suspension is then added a slight excess of methyl iodide and heated at 53° C. for 90 minutes. Evaporation of the solvent yields a residue which is dissolved in ethyl acetate, washed with water and dried over sodium sulfate. Removal of ethyl acetate and taking up the residue with cyclohexane yields a product which is used for the further step. A sample of the acetaldehyde methyl(6-morpholino-3-pyridazinyl)hydrazone crystallized from ethyl ether melts at 136° C.

The acetaldehyde hydrazone is hydrolyzed according to the procedure of method G described by G. Pifferi et al. in J. Med. Chem., 18, 741 (1975). The 3-(1-methylhydrazino)-6-morpholino-pyridazine dihydrochloride monohydrate, crystallized from methanol, melts at 183°-190° C. (softening at 177° C.).

EXAMPLE 26

N-(2,5-Dimethyl-1H-pyrrol-1-yl)-4-(4-hydroxypiperidino)-1-phthalazineamine

To a solution of 1.5 g (5.8 m mol) of 1-hydrazino-4-(4-hydroxypiperidino)-phthalazine in 60 ml of acetic acid, 0.79 g (6.9 m mol) of 2,5-hexanedione are added and the mixture is heated at 67° C. for 3 hours. After evaporation of the solvent the residue is neutralized with aqueous sodium bicarbonate and extracted with ethyl acetate. The organic solution is chromatographed through a silicagel column using ethyl acetate as the eluent.

Yield 0.5 g (26%) of the product of the title which melts at 180°-185° C.

Elemental analysis, I.R. and N.M.R. data confirm the assigned structure.

The 1-hydrazino-4-(4-hydroxypiperidino)-phthalazine is prepared by reacting 1,4-dichlorophthalazine with 4-hydroxypiperidine to yield 1-chloro-4-(4-hydroxypiperidino)-phthalazine (m.p. 139°-142° C.) and then converting this latter to the corresponding hydrazino derivative by reaction with an excess of hydrazine hydrate. These reactions are carried out according to the procedure described in U.K. Pat. No. 1.157.642 for analogous hydrazino pyridazine derivatives.

The 1-hydrazino-4-(4-hydroxypiperidino)-phthalazine melts at 190°-192° C. (from isopropanol).

In the exploitation of the invention, the preferred administration route of the new compounds of this invention is per os in the form of capsules, tablets, troches, lozanges, granules, suspensions, syrups, elixirs or solutions. If desired, for severe cases, parenterally administrable dosage forms can also be prepared as injectable ampoules. The dosage forms for oral use are prepared by common procedures. Capsules, besides the active ingredient may contain pharmaceutically acceptable excipients, such as, for instance, dextrin, starch, lactose, cellulose derivatives, and magnesium stearate. Coated or hard shell capsules can also be prepared. Tablets may include inert diluents such as lactose, glucose and talk, granulating and disintegrating agents such as starch and alginic acid; binding agents; and lubricating agents such as magnesium stearate, talk etc. For example, a gelatin capsule suitable as a dose unit may contain 10 mg of the compound of example 3 or its hydrochloride, 1.5 mg of magnesium stearate and 118.5 mg of corn starch. Other possible oral dosage forms such as suspensions, syrups and elixirs are formulated as known in the art (see for instance the book "Remington's Pharmaceutical Sciences, 13th Ed. Mack Publishing Co. Easton, Pennsylvania) and may contain suspending agents, such as methyl cellulose, tragacanth or alginates; wetting agents such as polyoxyethylene sorbitan monoleate; and preservatives. The liquid solutions for both oral and parenteral use may contain antioxidants, preservatives, buffering agents, and dispersing or wetting agents. The solvents which may be employed generally are water or mixture of water and polihydric aliphatic alcohols. For instance, a suitable dose unit form for extemporaneous parenteral use may be prepared by dissolving the content of a lyophylized vial consisting of 3 mg of the compound of example 3 or its hydrochloride, 50 mg of mannitol and 0.5 mg of disodium edetate in 10 ml of water for injection.

In general, the antihypertensive effective amount of the novel compounds of this invention depend on several factors such as the particular compound administered, the body weight, the severity and the origin of the hypertensive disorders, the effects and the nature of other pharmacologically active substances which may be associated thereto in the treatment of the hypertension. In general, the treatment of hypertensive disorders with the new pyrrolyl-pyridazineamines of this invention may be started with low dosages which may be generally increased according to the individual response. The antihypertensive effective dosage in oral administration usually ranges from about 0.10 mg/kg to about 3 mg/kg, with the daily dosage of from about 0.25 mg/kg to about 2 mg/kg being preferred. In parenteral administration, the antihypertensive effective dosage generally ranges from about 0.01 mg/kg to about 1.5 mg/kg daily, the dosage range from about 0.03 mg/kg to about 1 mg/kg daily being preferred.

It is however clear that a dose beyond the above indicated ranges may also be employed depending on the individual conditions of the subject to be treated.

TABLE I

| R | $R_1$ | $R_2$ | $R_3$ | $R_4$ | $R_5$ | $R_6$ | $R_7$ | $R_8$ |
|---|---|---|---|---|---|---|---|---|
| $CH_3$ | H | H | $CH_3$ | H | $-C_2H_5$ | $-C_2H_5$ | H | H |
| $CH_3$ | H | H | $CH_3$ | H | $-CH_2-CH_2-CHOH-CH_2-CH_2-$ | | H | H |
| $CH_3$ | H | H | $CH_3$ | H | $-CH_2-CH_2-NH-CH_2-CH_2-$ | | H | H |
| $CH_3$ | H | H | $CH_3$ | H | $-CH_2-CH_2-N(CH_3)-CH_2-CH_2-$ | | H | H |
| $CH_3$ | H | H | $CH_3$ | H | $-CH_3$ | $-CH_2-CHOH-CH_3$ | H | H |
| $CH_3$ | H | H | $CH_3$ | H | $-CH_2-CH_2OH$ | $-CH_2-CH_2OH$ | H | H |
| $CH_3$ | H | H | $CH_3$ | H | $-CH_2-CH_2OH$ | $-CH_2-CHOH-CH_3$ | H | H |
| $CH_3$ | H | H | $-CH_3$ | H | $-CH_2-CH=CH_2$ | $-CH_2-CH=CH_2$ | H | H |
| $CH_3$ | H | H | $-CH_3$ | $-CH_2-CH_2-$ $-N(CH_3)_2$ | $-CH_2-CH_2-O-CH_2-CH_2-$ | | H | H |
| $CH_3$ | H | H | $CH_3$ | H | $-CH_2-CH_2-CH_2-CH_2-$ | | H | H |
| $CH_3$ | H | H | $CH_3$ | H | $-CH_2-CH_2-CH_2-CH_2-CH_2-$ | | H | H |
| $CH_3$ | H | H | $CH_3$ | H | $-CH_2-CH_2-O-CH_2-CH_2-$ | | H | H |
| $CH_3$ | H | H | $CH_3$ | $CH_3$ | $-CH_2-CH_2-O-CH_2-CH_2-$ | | H | H |
| $CH_3$ | H | H | $CH_3$ | H | $-CH_2-CH(CH_3)-O-CH(CH_3)-CH_2-$ | | H | H |
| $CH_3$ | H | H | $CH_3$ | H | $-CH_2-CHOH-CH_3$ | $-CH_2-CHOH-CH_3$ | H | H |
| $C_2H_5$ | H | H | $C_2H_5$ | H | $-CH_2-CH_2-O-CH_2-CH_2-$ | | H | H |
| $CH_3$ | H | H | $CH_3$ | $-COCH_3$ | $-CH_2-CH_2-O-CH_2-CH_2-$ | | H | H |

TABLE I-continued

| R | $R_1$ | $R_2$ | $R_3$ | $R_4$ | $R_5$ | $R_6$ | $R_7$ | $R_8$ |
|---|---|---|---|---|---|---|---|---|
| $CH_3$ | H | H | $CH_3$ | H | —$CH_2$—$CH_2$—O—$CH_2$—$CH_2$— | | —CH=$CH_2$—CH=$CH_2$— | |
| $CH_3$ | H | H | $CH_3$ | H | —$CH_2$—$CH_2$—$OCH_3$ | —$CH_2$—$CH_2OCH_3$ | H | H |
| $CH_3$ | H | H | $CH_3$ | H | —$CH_2$—$CH_2$—$OC_2H_5$ | —$CH_2$—$CH_2$—$OC_2H_5$ | H | H |
| $CH_3$ | H | H | $CH_3$ | H | —$CH_3$ | —$CH_2$—$CH_2OCH_3$ | H | H |
| H | H | H | H | H | —$CH_2$—$CH_2$—O—$CH_2$—$CH_2$— | | H | H |
| $CH_3$ | $CH_3$ | $CH_3$ | $CH_3$ | H | —$CH_2$—$CH_2$—$OCH_3$—$CH_2$— | | H | H |
| $CH_3$ | H | $CH_3$ | H | H | —$CH_2$—$CH_2$—O—$CH_2$—$CH_2$— | | H | H |
| $CH_3$ | H | H | $CH_3$ | H | —$CH_2$—$CH_2$—S—$CH_2$—$CH_2$— | | H | H |
| $CH_3$ | H | H | $CH_3$ | H | —$CH_2$—$CH_2OCOCH_3$ | —$CH_2$—$CH_2OCOCH_3$ | H | H |
| $CH_3$ | H | H | $CH_3$ | H | —$CH_3$ | —$C_6H_5$ | H | H |
| $C_2H_5$ | $CH_3$ | $CH_3$ | $C_2H_5$ | H | —$CH_2$—CHOH—$CH_3$ | —$CH_2$—CHOH—$CH_3$ | H | H |
| $CH_3$ | H | H | $CH_3$ | H | —$CH_2$—$CH_2$—N[(2—$OCH_3$)$C_6H_4$]—$CH_2$—$CH_2$— | | H | H |
| $CH_3$ | H | H | $CH_3$ | H | —$CH_2$—$CH_2$—N[(4—Cl)$C_6H_4$]—$CH_2$—$CH_2$— | | H | H |
| $CH_3$ | H | H | $CH_3$ | H | —$CH_2$—$CH_2$—N[(3—$CH_3$)$C_6H_4$]—$CH_2$—$CH_2$— | | H | H |
| $CH_3$ | H | H | $CH_3$ | H | —$CH_3$ | —$CH_2$[(3,4—$OCH_3$)$C_6H_3$] | H | H |
| $CH_3$ | H | H | $CH_3$ | H | $CH_3$ | —$CH_2$—$CH_2$[(3,4—$OCH_3$)$C_6H_3$] | H | H |
| $CH_3$ | H | H | $CH_3$ | H | $CH_3$ | —$CH_2$—[(3,4,5—$OCH_3$)$C_6H_2$] | H | H |
| $CH_3$ | H | H | $CH_3$ | —$COC_2H_5$ | —$CH_2$—$CH_2$—O—$CH_2$—$CH_2$— | | H | H |
| $CH_3$ | H | H | $C_2H_5$ | H | —$CH_2$—$CH_2$—N[(3,4—$OCH_2O$)$C_6H_3$]—$CH_2$—$CH_2$— | | H | H |
| $CH_3$ | H | H | $CH_3$ | $C_2H_5$ | —$CH_2$—$CH_2$—O—$CH_2$—$CH_2$— | | —CH=CH—CH=CH— | |
| $CH_3$ | H | H | $CH_3$ | H | —$CH_2$—$CH_2$—$CH_2$—$CH_2$— | | —CH=CH—CH=CH— | |
| $CH_3$ | $H_3$ | H | $CH_3$ | H | —$CH_2$—$CH_2$—$CH_2$—$CH_2$—$CH_2$— | | —CH=CH—CH=CH— | |
| $CH_3$ | H | H | $CH_3$ | H | —$CH_2$—$CH_2$—MH—$CH_3$—$CH_2$— | | —CH=CH—CH=CH— | |
| $CH_3$ | H | H | $CH_3$ | H | —$CH_2$—$CH_2$—$NCH_3$—$CH_2$—$CH_2$— | | —CH=CH—CH=CH— | |
| $CH_3$ | H | H | $CH_3$ | H | —$CH_2$—$CH_2$—N($CH_2$—$C_6H_5$)—$CH_2$—$CH_2$— | | H | H |
| $CH_3$ | H | H | $CH_3$ | H | —$CH_2$—$CH_2$—N[$CH_2$—$CH_2$(3,4—$OCH_3$)$C_6H_3$]$CH_2$—$CH_2$— | | H | H |
| $CH_3$ | H | H | $CH_3$ | $COCF_3$ | —$CH_2$—$CH_2$—O—$CH_2$—$CH_2$— | | H | H |
| $CH_3$ | H | H | $CH_3$ | —$CH_2$—$CH_2$—$N(C_2H_5)_2$ | —$CH_2$—$CH_2$—O—$CH_2$—$CH_2$— | | H | H |

We claim:
1. A novel pyrrolyl-pyridazineamine derivative of the formula

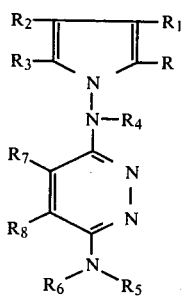

wherein R, $R_1$, $R_2$, $R_3$, may be the same or different and are independently selected from hydrogen and lower alkyl; $R_4$ represents hydrogen, lower alkyl, lower alkylamino-lower alkyl, di-lower alkylamino-lower alkyl, lower alkanoyl, halo-lower alkanoyl, carbo(lower alkoxy) or carbobenzyloxy; $R_5$ and $R_6$ each independently represent lower alkyl, hydroxy-lower alkyl, lower alkoxy-lower alkyl, lower alkanoyloxy-lower alkyl, lower alkenyl, phenyl, substituted phenyl, phenyl-lower alkyl and substituted phenyl-lower alkyl or taken together with the adjacent nitrogen atom represent a saturated 5–6 membered heterocyclic ring which may contain a further heteroatom selected from O, N and S, and which may bear 1 to 2 substituents selected from lower alkyl, phenyl, substituted phenyl, phenyl-lower alkyl, substituted phenyl-lower alkyl, hydroxy, hydroxy-lower alkyl and lower alkanoyloxy; $R_7$ and $R_8$ represent hydrogen atoms or, taken together, a 1,3-butadienylene radical forming a benzo system fused with the pyridazine ring; and its pharmaceutically acceptable acid addition salts.

2. A compound of claim 1 wherein $R_1$ and $R_2$ are both hydrogen, R and $R_3$ are independently selected from hydrogen, methyl and ethyl; $R_4$ represents hydrogen, methyl or acetyl; $R_5$ and $R_6$ each independently represent lower alkyl, lower alkenyl, hydroxy-lower alkyl, lower alkoxy-lower alkyl or taken together with the adjacent nitrogen atom represent a pyrrolidine, piperidine, morpholine, thiomorpholine and piperazine ring which may be optionally substituted with lower alkyl or hydroxy on the carbon atom moiety of said rings and with lower alkyl, phenyl and methoxyphenyl on the second nitrogen atom of the piperazine ring; $R_7$ and $R_8$ represent both hydrogen or, taken together, 1,3-butadienylene; and its pharmaceutically acceptable acid addition salts.

3. A compound of claim 1 wherein $R_1$ and $R_2$ are both hydrogen; R and $R_3$ are selected from hydrogen, methyl and ethyl, $R_4$ represents hydrogen, methyl or acetyl; $R_5$ and $R_6$ represent methyl, ethyl, allyl, hydroxyethyl, hydroxypropyl, methoxyethyl, ethoxyethyl or, taken together with the adjacent nitrogen atom represent pyrrolidine, piperidine, hydroxypiperidine, morpholine, 2,6-dimethylmorpholine, thiomorpholine, piperazine, 4-methylpiperazine, 4-(methoxyphenyl)piperazine; $R_7$ and $R_8$ represent both hydrogen; and its pharmaceutically acceptable salts.

4. A compound of claim 1 which is N-(2,5-dimethyl-1H-pyrrol-1-yl)-6-morpholino-3-pyridazineamine and its hydrochloride.

5. A compound of claim 1 which is 6-diethylamino-N-(2,5-dimethyl-1H-pyrrol-1-yl)-3-pyridazineamine.

6. A compound of claim 1 which is N-(2,5-dimethyl-1H-pyrrol-1-yl)-6-[N',N'-bis(2-methoxyethyl)amino]-3-pyridazineamine.

7. A compound of claim 1 which is N-(2,5-dimethyl-1H-pyrrol-1-yl)-6-[N',N'-bis(2-ethoxyethyl)amino]-3-pyridazineamine.

8. A method of treating hypertension in mammals which comprises administering to said mammals an antihypertensive effective amount of a compound of claim 1.

9. A pharmaceutically antihypertensive composition containing a compound of claim 1 as the active ingredient together with a carrier therefor.

10. A method as in claim 8 wherein the compound is selected from N-(2,5-dimethyl-1H-pyrrol-1-yl)-6-morpholino-3-pyridazineamine, 6-diethylamino-N-(2,5-dimethyl-1H-pyrrol-1-yl)-3-pyridazineamine, N-(2,5-dimethyl-1H-pyrrol-1-yl)-6-[N',N'-bis(2-methoxyethyl)amino]-3-pyridazineamine, N-(2,5-dimethyl-1H-pyrrol-1-yl)-6-[N',N'-bis(2-ethoxyethyl)amino]-3-pyridazineamine and their pharmaceutically acceptable acid addition salts.

11. A composition of claim 9 wherein the active ingredient is selected from N-(2,5-dimethyl-1H-pyrrol-1-yl)-6-morpholino-3-pyridazineamine, 6-diethylamino-N-(2,5-dimethyl-1H-pyrrol-1-yl)-3-pyridazineamine, N-(2,5l-dimethyl-1H-pyrrol-1-yl)-6-[N',N'-bis(2-methoxyethyl)amino]-3-pyridazineamine, N-(2,5-dimethyl-1H-pyrrol-1-yl)-6-[N',N'-bis(2-ethoxyethyl)amino]-3-pyridazineamine and their pharmaceutically acceptable acid addition salts.

* * * * *

UNITED STATES PATENT AND TRADEMARK OFFICE
CERTIFICATE OF CORRECTION

PATENT NO. : 4,247,551
DATED : January 27, 1981
INVENTOR(S) : Elvio Bellasio, et al.

It is certified that error appears in the above-identified patent and that said Letters Patent are hereby corrected as shown below:

Column 15 and 16, Table I-continued, under subtitle "$R_5$" should read -- $-CH_2-CH_2-NH-CH_3-CH_2-$.

Column 18, Claim 11, line 7, should read -- N-(2,5--dimethyl-1H-pyrrol-1-yl)-6-[N',N'-bis(2- --.

Signed and Sealed this

Twenty-fifth Day of August 1981

[SEAL]

Attest:

GERALD J. MOSSINGHOFF

Attesting Officer

Commissioner of Patents and Trademarks